United States Patent [19]

Thompson et al.

[11] Patent Number: 4,716,101
[45] Date of Patent: Dec. 29, 1987

[54] RAPID ENZYME ASSAY BY PRODUCT SELECTIVE BLOT

[75] Inventors: Gregory A. Thompson; Huw M. Davies, both of Davis, Calif.

[73] Assignee: Calgene, Inc., Davis, Calif.

[21] Appl. No.: 683,550

[22] Filed: Dec. 18, 1984

[51] Int. Cl.[4] ............... G01N 27/26; G01N 33/52; G01N 33/561

[52] U.S. Cl. ............... 435/4; 204/182.8; 204/299 R; 435/16; 435/288; 435/291; 435/810; 436/515; 436/516

[58] Field of Search ........... 436/515, 516, 810; 435/288, 291, 803, 805, 810, 4, 16, 18; 204/182.8, 299 R

[56] References Cited

U.S. PATENT DOCUMENTS

| | | | |
|---|---|---|---|
| 3,964,992 | 6/1976 | Krotz | 204/299 R |
| 4,243,753 | 1/1981 | Regnier et al. | 435/288 |
| 4,459,358 | 7/1984 | Berke | 436/170 |
| 4,541,910 | 9/1985 | Davis, III et al. | 204/182.8 |

OTHER PUBLICATIONS

Cooper, *The Tools of Biochemistry*, (1977), John Wiley & Sons, N.Y., pp. 155–156 and 212–216.
Southern (1979), J. Molec. Biol. 98:503–517.
Reinhart and Malamud (1982) Anal. Biochem., 123:229–235.
Smith and Summers (1980) Anal. Biochem., 109:123–129.
Towbin (1979), Proc. Natl. Acad. Sci., USA 76:4350–4354.
Alwine et al. (1979), Methods in Enzymology 68:220–242.
1984 Bio-Rad Catalog, pp. 19–20.
Somerville and Ogren (1980), Nature 286:257–259.
Siciliano et al. (1976), in: "Electrophoretic Techniques", Smith, ed., vol. 2, pp. 185–209, Wm. Heinemann Medical Books, Chicago.
Cardy et al. (1981), Techniques for Starch Gel Electrophoresis of Enzymes From Maize (*Zea mays* L.), Institute of Statistics Mimeograph Series No. 1317, N. Carolina Univ. Raleigh, N.C.
Davies et al. (1978), J. Chromatogr., 153:284–286.

*Primary Examiner*—Sidney Marantz
*Attorney, Agent, or Firm*—Bertram I. Rowland

[57] ABSTRACT

A method and assay kit for determining the presence of an enzyme in a sample are provided. A sample suspected of containing the enzyme is applied to an image gel, which may be any conventional material, typically agarose gel. The sample may first be subjected to electrophoresis, or may be detected directly using the present invention. The image gel includes an immobilized phase capable of binding a product of the enzyme but not the substrate. By exposing the enzyme to substrate, and drawing the resulting reaction mixtures through the image gel, only the product is bound in the image gel. The presence of enzyme may then be determined by detecting the product in the image gel. In addition to developing electrophoresis gels, the method of the present invention will find great use in screening a plurality of complex mixtures which have been separated by other conventional techniques.

18 Claims, 5 Drawing Figures

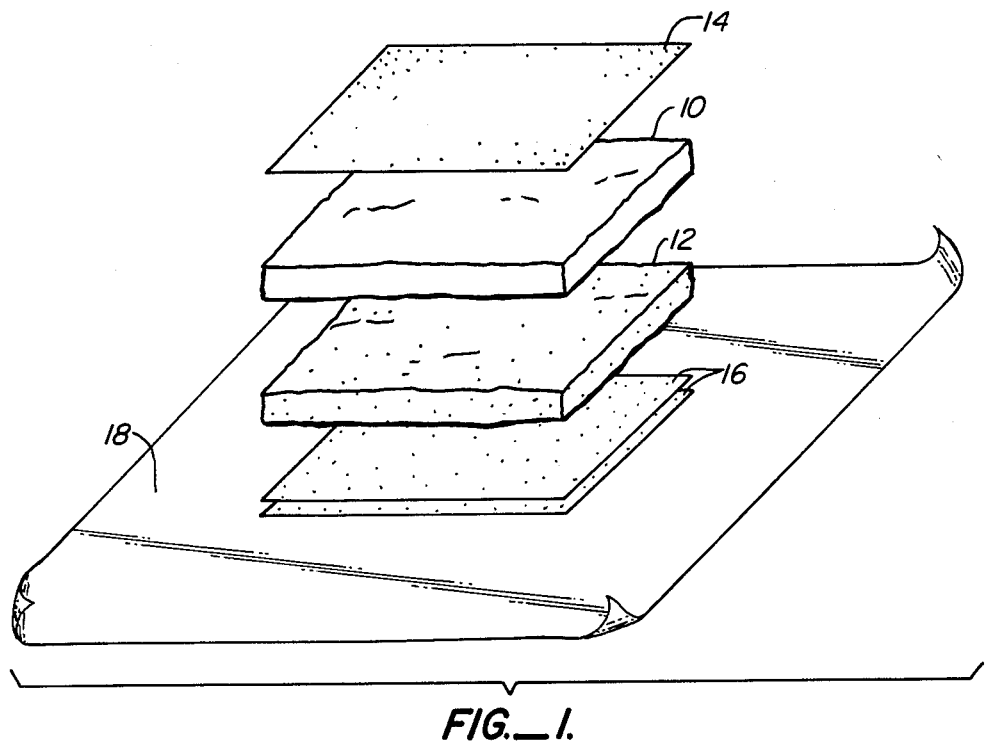
FIG._1.
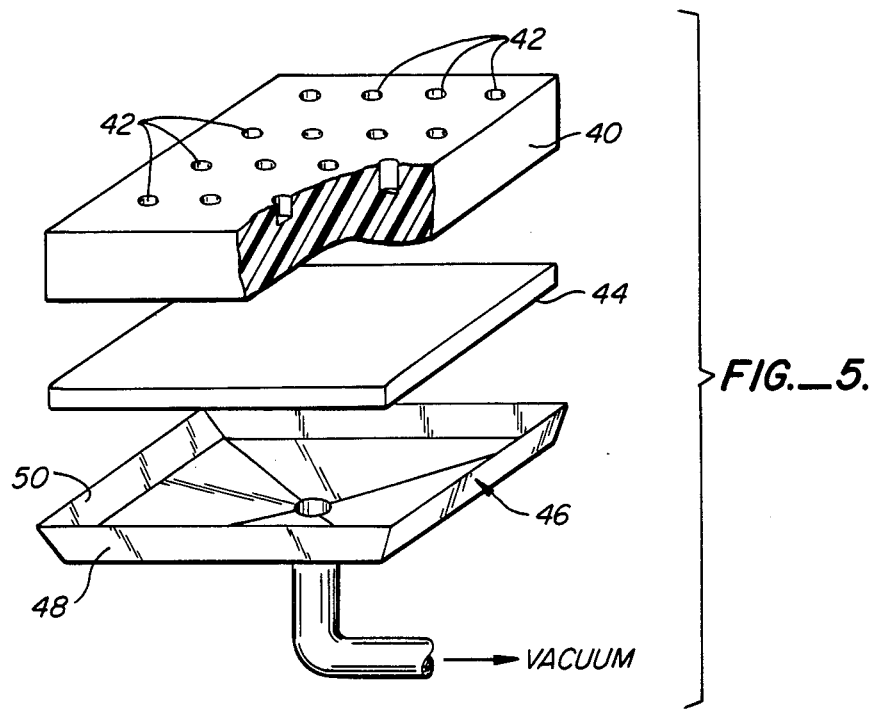
FIG._5.

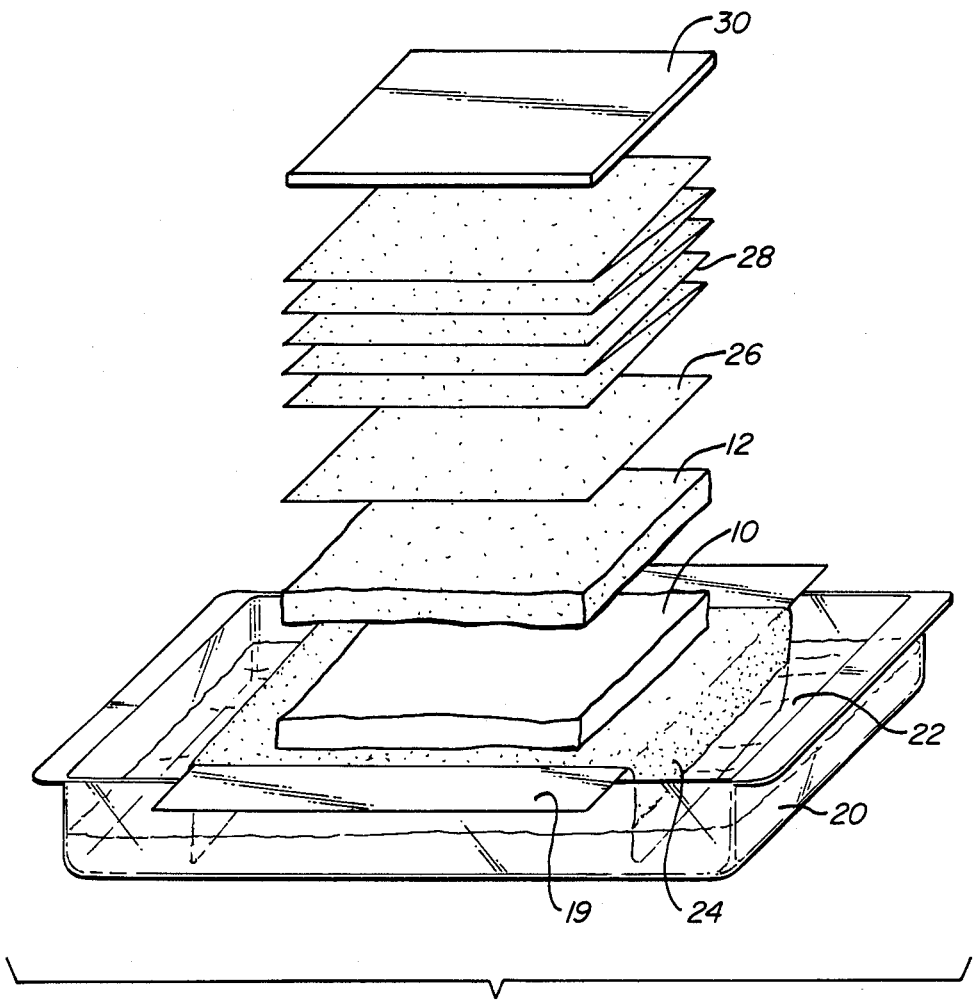
FIG._2.

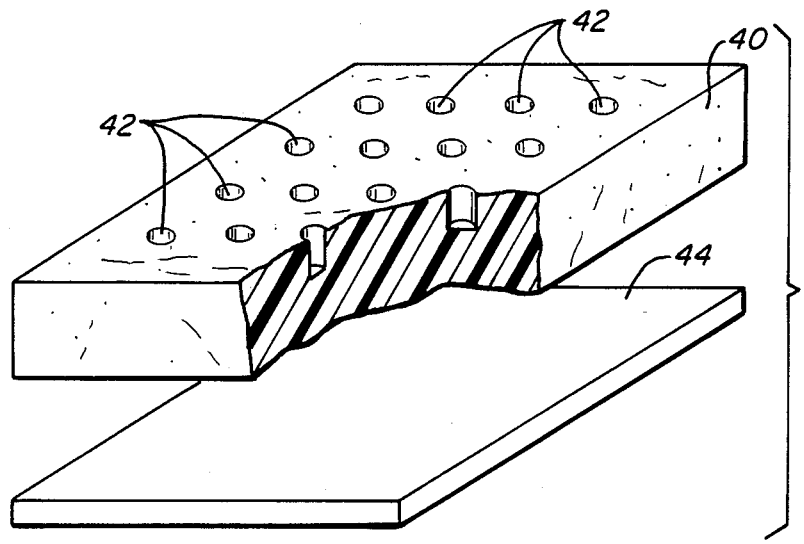
FIG._3.
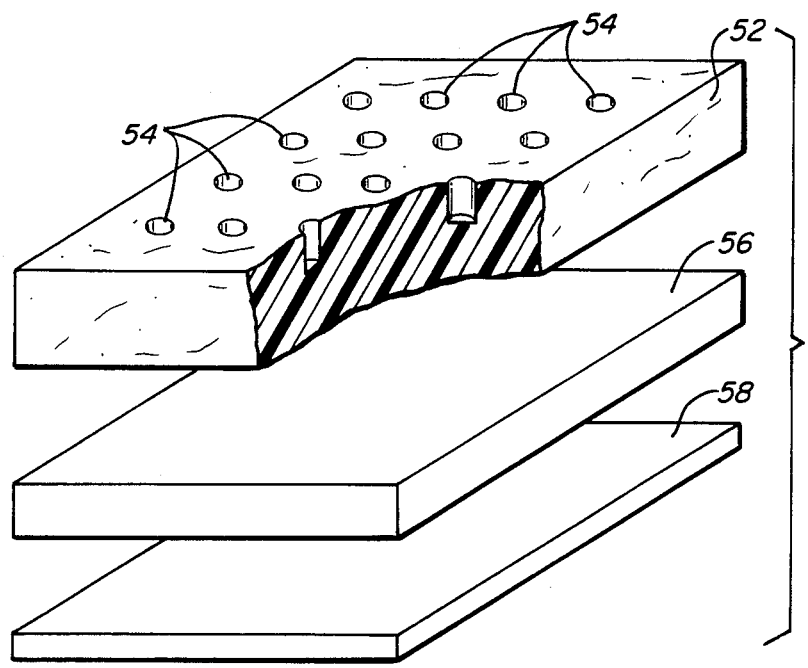
FIG._4.

RAPID ENZYME ASSAY BY PRODUCT SELECTIVE BLOT

BACKGROUND OF THE INVENTION

1. Field of the Invention

Methods for detecting the presence of particular enzymes found in complex biological mixtures are required under a variety of circumstances. While it is usually possible to separate the proteins found in such a mixture into a plurality of fractions based on size, molecular weight, net electrical charge, and the like, it still remains necessary to detect the enzyme of interest in one or more of the separated fractions.

A number of methods for the detection of enzymes exist. For example, detection can be accomplished immunologically using a labelled antibody specific for the enzyme. Such immunological detection, however, is limited by the availability of suitable antibodies. Enzyme detection can also be accomplished by exposing a protein fraction (or other sample suspected of containing the enzyme) to substrate for the enzyme. The presence of the enzyme in the fraction or sample can then be determined based on conversion of the substrate to product. This latter approach, although useful in many circumstances, requires that the substrate and product be distinguishable in a convenient and rapid manner. Many times, however, convenient detection reactions are not available and the difficulty in distinguishing the substrate from product makes this latter approach for identifying enzyme activity impractical.

For the above reasons, it would be desirable to provide an enzyme detection method which provides for separation of product from the substrate prior to detection of the product. In particular, it would be desirable to provide such a method which allows for simultaneous screening of a plurality of samples.

2. Description of the Prior Art

A number of blot transfer techniques exist for analyzing proteins and polynucleotides. For example, Southern blotting provides for transfer of polynucleotide fragments on an electrophoresis gel to cellulose nitrate filter paper by blotting a buffer solution through the gel and the filter. The polynucleotide of interest is then located on the filter by detection with a complementary DNA or RNA probe. See, Southern (1979) J. Molec. Biol. 98:503-517. An analogous technique, referred to as the Eastern or Native blot, has recently been developed for protein analysis. The proteins are separated by electrophoresis in a native gel using a non-denaturing buffer. The proteins are then transferred from the gel onto nitrocellulose by blot transfer. The protein of interest may then be identified immunologically. The method has been described by Reinhart and Malamud (1982) Anal. Biochem. 123:229-235; and Smith and Summers (1980) Anal. Biochem. 109:123-129. Other blotting techniques include the Western blot for detecting protein under extremely denaturing conditions (see, Towbin (1979) Proc. Natl. Acad. Sci. USA 76:4350-4354), and Northern blots for the detection of RNA on specially prepared reactive paper (Alwine et al. (1979) Methods In Enzymology 68:220-242). None of these blot detection methods provides for detection of an enzyme product. Assays for enzymatic activity have been performed using ion exchange columns where at least one of the substrate or product is ionic. See 1984 Bio-Rad Catalog, pp. 19-20, and the references cited on page 20. The use of ion exchange chromatography in the detection of glutamate synthase is described in Somerville and Ogren (1980) Nature 286:257-259. Various techniques for separating and visualizing enzymes in native gels are described in Siciliano and Shaw (1976) in: "Chromatographic and Electrophoretic Techniques," Smith, ed., vol. 2, pp. 185-209, Wm. Heinemann Medical Books, Chicago Illinois, and Cardy et al., (1981) Techniques for Starch Gel Electrophoresis of Enzymes from Maize (Zea mays L.), Institute of Statistics Mimeograph Series No. 1317, North Carolina State University, Raleigh, North Carolina. The fluorescent staining technique employed in the Experimental section hereinafter for visualizing product is described in Davies and Miflin (1977) J. Chromatogr. 153:284-286.

SUMMARY OF THE INVENTION

Methods and assay kits for detecting an enzyme in a sample are provided. The methods rely on exposing the sample to a substrate for the enzyme in a reaction mixture. By detecting the enzyme-catalyzed conversion of substrate to product, the presence of very low concentrations of enzyme in the sample may be determined. To enable selective detection of a product, the reaction mixtures are separated in an image gel which includes an immobile phase or ligand which is capable of selectively binding the product but not the substrate. Usually, the immobile phase will be an ion exchange resin dispersed throughout the image gel, although other binding substances, such as antibodies, lectins, and the like, may also find use.

The detection method of the present invention may be combined with conventional gel electrophoresis when analyzing complex protein mixtures. The protein mixture may be separated on an electrophoresis gel under conditions which do not denature the proteins, i.e., a native gel. After introducing appropriate substrate(s) to the electrophoresis gel, the resulting reaction mixture is transferred to the image gel by any suitable blotting technique, such as capillary blotting, vacuum-assisted blotting, or electroblotting. After washing the image gel to remove all traces of the substrate and other unbound substances, the image gel is exposed to desired detection reagents which will produce a visually detectable product. Alternatively, by employing a radiolabelled substrate, the resulting radiolabelled product may be detected in the image gel by autoradiography or liquid scintillation counting.

The detection method of the present invention may also be utilized to screen a plurality of samples for the presence of the enzyme of interest. Such samples may be the result of a previous separation step, e.g., chromatographic separation fractions, or may be unseparated. The samples are pre-reacted with substrate, typically in microtiter plates or separate test tubes, and transferred to the image gel in a predetermined, non-overlapping pattern. Conveniently, the image gel will include preformed wells for receiving the samples. For fluorometric detection, it is desirable to employ an application gel which is free of the immobile phase. The application gel includes preformed wells for receiving the samples and is laminated to the image gel. The samples are transferred from the application gel to the image gel (which is without wells) by blotting. The application gel acts to filter out background fluorescing compounds which might interfere with detection and assures that the "spots" transferred to the image gel are distinct and free from a corona caused by radial diffusion of the reaction mixture. The presence of product in the image gel is determined as just described.

BRIEF DESCRIPTION OF THE DRAWINGS

FIG. 1 is a blotting system for introducing substrate to an electrophoresis gel and for transferring the resulting reaction mixtures from the electrophoresis gel to an image gel (Method B in the Experimental section).

FIG. 2 is an alternate embodiment of the blotting system.

FIG. 3 is a detection system suitable for radiometric screening of a plurality of pre-reacted samples (Method A as described in the Experimental section).

FIG. 4 is a detection system suitable for fluorescent screening of a plurality of pre-reacted samples (Method A as described in the Experimental section).

FIG. 5 illustrates a blotting system which relies on vacuum-enhanced transfer of the reaction mixtures from an application gel to an image gel.

DESCRIPTION OF THE SPECIFIC EMBODIMENTS

The present invention provides a convenient and rapid method for analyzing complex biological mixtures for the presence of particular enzymes based on their respective enzymatic activities. The enzymes are identified based on their ability to convert substrate into a detectable product, and the improvement lies in the separation of the product from the substrate using convenient blotting techniques prior to detection of the product. Thus, an enzyme product which is very closely related to its substrate may be detected without the possibility of confusion with the substrate.

The method of the present invention employs either a one- or a two-gel system where a sample suspected of containing the enzyme may be pre-reacted with substrate or reacted in one of the gels, as will be described in detail hereinafter. The method is useful for detecting bands of enzymes which have been separated by gel electrophoresis, in which case the reaction with substrate is carried out in the electrophoresis gel itself. The reaction mixture including substrate and product (if any), is transferred to an image gel incorporating an immobile phase or ligand capable of selectively binding enzyme reaction product but not substrate. The reaction mixture will thus be localized on the image gel along a band corresponding to the enzyme to be detected in the electrophoresis gel. Following a wash step to remove unbound substrate and other potentially interfering substances, the image gel is developed, typically by radiometric or fluorescent techniques, to reveal the bound product, if any.

It should be appreciated that the enzyme may require more than one substrate to produce the detectable product, in which case it is necessary only that the gel system separate the product from those substrates which might be confused with the product. For example, when the product is detectable by means of a label (such as a radiolabel) which is introduced to the product by reacting a labelled substrate, it is necessary only that the gel system separate the labelled substrate from the product. Any unlabelled substrate(s) which may participate in the reaction need not be separated from the product since they are not detectable. It is also possible that more than one product may be produced by the reaction system utilized for detection of the enzyme of interest. For the sake of simplicity, however, the specification and claims will refer to only a single substrate and single product. The present invention, however, encompasses multiple substrate and/or multiple reaction systems as well.

The method of the present invention is also useful for screening a plurality of samples which have been pre-reacted with substrate. The pre-reacted samples are applied to the image gel (either directly or by use of an application gel as described hereinafter) in a predetermined, non-overlapping pattern, and any product present in the reaction mixtures will be localized on the image gel at positions corresponding to the initial locations of the samples, i.e, in a two dimensional array corresponding to the initial application pattern of the samples.

Sample screening according to the present invention is particularly useful during conventional separation or purification procedures, e.g., liquid chromatography, affinity chromatography, high speed centrifugation, salt fractionation, and the like. The manner of separation, if any, is not critical and will be dependent upon the nature of the complex mixture and the enzyme to be detected.

Transfer of the reaction mixture from the electrophoresis gel to the image gel is effected by juxtaposing one face of the electrophoresis gel against one face of the image gel, and blotting. Care is taken to assure that close contact is made across the entire interface, particularly assuring that no bubbles or other discontinuities are formed. Conveniently, electrophoresis gel and image gel may be laminated together prior to introduction of substrate. Then, by introducing substrate in a suitable buffer and drawing the substrate buffer through the electrophoresis gel and into the image gel, the substrate reaction and localization of product in the image gel may be accomplished in one step. The substrate buffer may be drawn through the laminate of the electrophoresis gel and image gel in a variety of ways. For example, the open face of the electrophoresis gel may be contacted with a reservoir of the substrate buffer, and the buffer drawn through both the electrophoresis gel and image gel by either blotting or by using a vacuum placed on the open face of the image gel. In some cases, electrophoretic transfer (electroblotting) of the reaction mixture from the electrophoresis gel to the image gel may find use.

The nature of the electrophoresis gel is not critical. Any conventional electrophoresis gel may be utilized, depending primarily on the expected molecular weight of the enzyme. Generally, starch gels and agarose gels will be utilized for separating relatively large molecules, while polyacrylamide gels will be used for separating relatively smaller enzymes. It is important that the electrophoresis gel be free from substances, such as detergents, which would denature the enzymes, since detection relies on retention of enzymatic activity. Such gels are generally referred to as native gels. Gels will typically be formed in flat sheets or plates having a thickness in the range from about 1 to 5 mm, typically from 1 to 2 mm, and lengths and widths in the range of 5 to 20 cm. Suitable materials for forming agarose gels may be obtained from Bio-Rad Laboratories, Richmond, California, or from FMC Corporation, Marine Colloids Division, Rockland, Maine, under the tradenames Sea Kem®, Sea Plaque®, and Sea Prep®. Materials for forming polyacrylamide gels are available from Bio-Rad Laboratories, Richmond, California. Suitable potato starch for forming gels is available from a number of commercial suppliers.

The image gel includes an immobile phase which is capable of selectively binding the product but not the substrate or other potentially interfering substances. Thus, as the reaction mixtures pass through the image gel, the product (if any) will be selectively bound within the image gel while the substrate is free to pass therethrough. After transfer is complete, the image gel may be removed and thoroughly washed to remove substrate and other unbound substances. Conventional techniques for detecting the bound product may then be utilized, as discussed in detail hereinbelow. The presence of the product in the gel is indicative of the enzyme of enzymatic activity in the associated sample.

The image gel may be formed from any of the gel materials suitable for the electrophoresis gel, as just described. Specifically, these materials include polyacrylamide gels, agarose gels, starch gels, and the like. The primary difference in the image gel is the inclusion of an immobilized phase which is capable of selectively binding the product but not the substrate. The immobilized phase is usually dispersed evenly throughout the image gel so that the product will be bound at whatever point it enters the image gel. Alternatively, it is possible to localize the immobilized phase at certain preselected positions in order to clearly delineate the detection zones in the image gel, as will be described further hereinafter. When the immobilized phase is localized, it will be necessary to locate the reaction mixtures in the application gel in a pattern which corresponds to the pattern of immobilized phase in the image gel. In this way, even if the reaction mixtures diffuse radially from their initial positions in the application gel, the product will only be bound within a well defined area in the image gel. Such well defined detection zones facilitate automatic detection of product in the image gels, such as by scanning densitometers, as will be described in greater detail hereinafter. The image gels will normally be rectangular with peripheral dimensions in the range from about 5 to 20 cm, with a thickness in the range from about 2 to 5 mm.

The immobilized phase capable of selectively binding the product will normally be an ion exchange material, which may be any natural clay mineral or synthetic resin in which immobile hydrated ions initially bound to the exchange material may be exchanged for charged functionalities on the product molecules. The ion exchange material may be anionic or cationic in nature, depending on the charge distribution on both the substrate and the product as well as on the pH at which the separation is carried out. The separation pH is selected to impart a differing net charge on the substrate and product molecules. Specifically, the pH will be such that the product molecules will have a net positive or negative charge, while those of the substrate will be uncharged or have the opposite charge. The ion exchange material may then be selected to bind the product but not the substrate, i.e., an anionic exchange material will be selected to bind a negatively charged product while a cationic exchange material will be selected to bind a positively charged product. Specific examples are provided in the Experimental section hereinafter.

Suitable cationic exchange resins include Dowex ®-50, while suitable anionic exchange resins include Dowex ®-1. Analytical grade forms of both these materials are available as AG 50W-X8 and AG 1-X8, respectively, available from Bio-Rad Laboratories, Richmond, California. The resins are available as fine beads and may be added to the image gel at the time it is poured. For most applications, an agarose gel such as Sea Kem ® is suitable for forming the image gel. For image gels where a radioactive product is to be detected by liquid scintillation counting, a low melt agarose gel, such as Sea Plaque ®, is suitable. The agarose beads are suspended in water at a concentration from about 0.5 to 5 weight percent, usually about 1.5 weight percent. After melting the agarose beads by boiling, the ion exchange resin beads suspended in water are added to the hot liquid to reach the desired concentration, usually from about 5 to 10 weight percent. The resulting mixture is then cooled over ice with constant stirring until the temperature reaches about 5° C. above the gelling temperature (45° C. for Sea Kem ® and 26° C. for Sea Plaque ®). The mixture may then be poured into a standard gel form and allowed to harden. The image gel is then ready for use, although for fluorometric detection, it will often be desirable to pour an application gel directly over the image gel, as described more fully hereinafter.

The electrophoresis gel and image gel are laminated together after the electrophoresis is complete, typically as illustrated in FIG. 1. The electrophoresis gel 10 is physically placed over the image gel 12 and pressure is applied evenly over the upper surface of the reaction gel to eliminate air bubbles and assure complete contact between the two gels. Substrate is introduced to the electrophoresis gel 10 by placing a bibulous layer 14 thereover. The bibulous layer 14, typically filter paper or other absorbent material, is soaked in a buffered substrate solution at an appropriate pH for the enzymatic reaction to occur. The substrate solution will permeate downward through both the electrophoresis gel 10 and image gel 12 and finally into a pair of absorbent layers 16. The absorbent layers 16 act to blot the substrate solution which enhances the flow through both gel layers. To avoid loss of the substrate solution, the resulting blotting assembly is wrapped in a water impermeable layer 18, typically a plastic wrap such as Saran ® wrap.

As the substrate buffer passes downward through the electrophoresis gel 10, reaction occurs between the substrate and enzyme (if any), resulting in the formation of product. The product will flow with the substrate into the image gel 12, where the product is bound. After a sufficient time for the enzymatic reaction to occur and for a product to be transported into the image gel 12, the blotting assembly may be disassembled and the image gel removed. The image gel will then be thoroughly washed to remove substantially all of the substrate and other unbound substances. The wash solution will be at a pH which allows continued binding of the product, while assuring that the substrate will be washed away. The image gel 12 is now ready for detection of the bound product, as will be described in detail hereinafter.

An alternate blotting assembly suitable for electrophoresis gels is illustrated in FIG. 2. There, the electrophoresis gel 10 is placed on a plastic support plate 19 which is located over a dish 20 which is filled with water or washing buffer 22 and may include substrate. A bibulous layer 24 which has been soaked in substrate solution is draped over the plate 19 and acts to draw the water solution upward therethrough by capillary action. The image gel 12 is placed on top of the electrophoresis gel 10 and a plurality of absorbent layers 26 and 28 are placed on top of the image gel 12. The absorbent layer 26 is typically filter paper, while the multiple layers 28 have a higher absorptive capacity, usually being paper towels or other absorbent paper. A second plastic plate 30 is placed on top of the assembly, typically having a weight placed on top thereof to hold the assembly together. The blotting action of the paper towels assures that a relatively large amount of water is able to flow through both the electrophoresis gel 10 and image gel 12. The large flow of water enhances the transfer of product from the electrophoresis gel to the image gel, which facilitates detection, particularly of very low concentrations of enzyme.

Embodiments of the blotting apparatus suitable for screening multiple, discrete samples are illustrated in FIGS. 3–5. These embodiments are particularly suited for the screening of a plurality of samples which have been previously separated by liquid chromatography, or other separation techniques, or for phenotype screening in genetic analysis. In the embodiment of FIG. 3, an image gel 40 includes a plurality of reaction wells 42 formed in one surface thereof. The reaction wells 42 extend downward into the gel 40, but terminate at about its middle. The samples to be assayed are pre-reacted with substrate, typically in microtiter wells or separate test tubes, and then added directly to the wells 42. The image gel 40 is cast over an agarose support gel 44, and the reaction mixtures may be drawn into the image gel using a vacuum assembly, as illustrated in FIG. 5. Such a vacuum assembly may also find use in drawing the reaction mixture from an electrophoresis gel to an image gel, as described previously.

An alternate embodiment for screening multiple samples is illustrated in FIG. 4. An application gel 52 having wells 54 is formed from any of the gel materials described above, usually agarose, but is free from the immobilized phase. The application gel 52 is formed by pouring directly over an image gel 56. An agarose support gel 58 is provided for mechanical support. The embodiment of FIG. 4 is particularly suited for fluorescent screening where fluorescing contaminants must be filtered out prior to introduction to the image gel. The application gel 52 provides the filtering function as well as assuring that the rection mixture is transferred to the image gel as discrete spots free from radial diffusion. The assay is then performed in the same manner as for the embodiment of FIG. 3.

To assist in transferring the reaction mixtures into the image gels 40 (FIG. 3) and 56 (FIG. 4), a vacuum assembly 46 (FIG. 5) is utilized. The vacuum assembly 46 includes a nozzle 48 having a peripheral flange 50 which receives the lower end of the support gel 44 or 58. Thus, when the image gel 40 and support gel 44 are placed in the vacuum assembly 46, a vacuum is drawn over the entire lower face of the separation gel. This vacuum will act to draw the reaction mixtures downward through the application gel 52 (if present) and into the image gel 40 or 56.

Once the product has been bound to the immobile phase in the image gel, and the image gel washed to remove substrate and other unbound substances, it is necessary to detect the bound product. Such detection may be accomplished in a variety of manners, including colorimetrically, fluorescently, and radiometrically. Radiometric detection is the most sensitive, but is limited by the need to employ and utilize radioactive materials. The detection, however, is quite straight forward. A radio-labelled substrate containing a radionuclide such as $^3H$, $^{14}C$, $^{32}P$, or the like is used. The radio-labelled substrate is converted into radio-labelled product only if the enzyme is present. Thus, when the reaction mixture is passed through the image gel, radioactivity will be bound only if product is present. Radioactivity in the gel may then be detected in a conventional manner using either an autoradiogram, scintillation counting, or the like, and the presence of enzyme thereby determined.

Many suitable colorimetric and fluorometric detection schemes exist, depending on the nature of the substrate and product. For example, o-phthalaldehyde (OPA) may be used to detect amino acids or other molecules having reactive amino groups. The separation gel may be exposed to low concentrations of OPA in a suitable buffer. The reaction between OPA and the product will then cause fluorescence under light (254 nm). Other examples are well known in the art.

The following experiments are offered by ways of illustration, not by way of limitation.

EXPERIMENTAL

The following abbreviations are used:
EDTA - ethylene diamine tetraacetic acid
TCA - trichloroacetic acid

MATERIALS AND METHODS

Chemicals

All chemicals were of analytical reagent standard or of the best grade available. Dithiothreitol was a special high purity grade from Calbiochem-Behring. L-Glutamine obtained from BDH Chemicals (Poole, Dorset, UK) was purified by passage through AG 1-X8 acetate to remove residual glutamic acid before use. Ion exchange resins used in blots were analytical grades of Dowex (AG 1-X8 acetate, 200–400 mesh and AG 50W-X8 H+, 200–400 mesh) obtained from Bio-Rad, Richmond, California.

L- [$^{14}C(U)$]Glutamine (250 mCi per mmol),
α-[$^{14}C(U)$]ketoglutaric acid (258 mCi per mmol),
L-[$^{14}C(U)$]glutamic acid (294 mCi per mmol), and
Aquasol-2 cocktail were purchased from New England Nuclear, Boston, Massachusetts.

Enzyme Samples

Glutaminase (Type V from *E. coli*, EC 3.5.1.2) was obtained from Sigma Chemical Co., St. Louis, Missouri. Crude extracts of glutamate synthase (GOGAT, EC 1.4.7.7) from maize (Zea Mays, Northrup-King hybrid PX74K) were prepared by homogenization of deveined leaves of three-weak old corn seedlings in a mortar and pestle at 4° C. in 2 ml per g fresh weight of 80 mM potassium phosphate, pH 7.5, containing 10 mM dithiothreitol, 1 mM EDTA, 1 mM phenylmethylsulfonylfluoride, and 20% (w/v) glycerol. Low molecular weight compounds from the plant were removed by passage through a column of Sephadex ® G-25 (medium) by centrifugation as taught by Penefsky (1977) J. Biol. Chem. 252:2891–2899.

Enzyme Assays

Glutaminase reactions were run in microcentrifuge tubes at 37° C. in mixtures containing L-glutamine (5 μmol), sodium acetate, pH 4.9 (20 μmol), and *E. coli* glutaminase (40 to 80 mU) in a total volume of 250 μl. Reactions were initiated by addition of enzyme and terminated after 5, 10, or 20 min by addition of 70 μl 10% (w/v) TCA. For zero-time measurements, the TCA was added before the enzyme.

Glutamate synthase reactions were run at 30° C. in mixtures containing L-glutamine (2.5 μmol), α-ketoglutarate (2.5 μmol), aminooxyacetate (2.5 μmol), methyl viologen (400 μg), imidazole-HCl, pH 7.5 (20 μmol), extract from corn leaves (50 to 100 μl), and sodium dithionite (0.8 mg as an 80 mg per ml solution in 1 M sodium bicarbonate) in a final volume of 250 μl. Reactions were initiated by adding dithionite and were terminated after 15, 30, or 60 min by addition of 70 μl 10% (w/v) TCA. For zero-time measurements, TCA was added before the dithionite.

Product-selective Blotting

Two methods of productive-selective blotting are utilized, as summarized in Table 1, below. Method A, in which multiple samples are applied to the gel system in preformed wells (FIGS. 3 and 4), is suitable for the detection of enzyme activity in a large number of samples. Method B uses the same technology without preformed wells to detect bands of enzyme activity in a native electrophoresis gel (FIG. 1). Details of each method are given below.

TABLE 1

| Method A | | Method B | |
|---|---|---|---|
| Step 1a | Enzyme reactions performed in test tubes or microtiter plate. | Step 1b | Form laminate containing absorbent paper, image gel, electrophoresis gel, and filter paper saturated with substrate (see FIG. 1). |
| Step 2a | Deproteinize (optional) and apply aliquot to well-containing application or image gel (see FIGS. 3 or 4). | Step 2b | Enzyme reaction in electrophoresis gel. |
| Step 3 | Apply suction to draw products into the image gel (see FIG. 5). | | |
| Step 4 | Wash image gel. | | |
| Step 5 | Stain or count radioactivity in the image gel. | | |

Method A

Casting the Laminate

Gel laminates were constructed for use in enzyme screening assays. First, a 2 mm thick support layer of 1.5% (w/v) agarose was cast. This layer served to protect against loss of resin particles from the image gel during later steps when the gel tended to become dry and brittle. After this layer had cooled, a 4 mm thick image gel containing ion exchange resin was cast over it. The image gel was prepared by adding packed wet ion exchange resin to melted agarose to make a mixture which contained 71 mg resin/ml AG 1X8 acetate or 49 mg/ml AG 50W-X8 $H^+$ in 0.75% (w/v) agarose and then casting when the mixture had cooled to 5° C. above its gelling temperature (45° C. for normal agarose; 26° C. for low-melt agarose). Casting while the mixture was too hot resulted in uneven distribution of the resin in the gel. Finally, a 9 mm thick application layer containing 7 mm deep wells and consisting of 1.5% (w/v) agarose was cast over the image gel. The wells were formed in this layer using a template constructed from a standard microtiter plate with tight fitting glass rods (2.8 × 0.6 cm or 2.8 × 1.0 cm) inserted in the wells of the plate. The depth of the wells was determined by placing appropriately longer support rods in the corner positions from which the template was suspended in the gel.

The use of an application layer rather than wells cast directly in the image gel had two advantages. Firstly, it led to visualization of product in discrete spots rather than as rings around the outside of each well, thus enabling quantitation by scanning densitometry. Secondly, in fluorimetric product-selective blots, the application layer acted as a filter to remove pigments in crude enzyme preparations which interfered with fluorescence measurements. However, where product was measured by liquid scintillation counting, samples were applied directly to wells molded in the image gel. In these cases, the thickness of the image gel, composed of 71 mg/ml AG 1-X8 acetate or 49 mg/ml AG 50W-X8 $H^+$ in 1.5% (w/v) low-melt agarose, was increased to 13 mm with 7 mm deep wells.

Blotting and Detection

Reaction mixtures were centrifuged at 4° C. for 5 min in a Beckman Instruments (Fullerton, CA) Model B Microfuge, and 64 μl aliquots of the supernatant fluid were adjusted to pH 7.0 with 1 M NaOH. Each aliquot was then applied to a separate well in the application layer of a gel laminate and drawn into the gel by suction on a large Buchner funnel. The image gel was then separated from the application and support layers and washed by gentle agitation in eight 500 ml changes of $H_2O$ (15 min/change).

Product was visualized by staining the gel with o-phthalaldehyde using the reagent formulation of Davies and Miflin (1978) J. Chromatogr. 153:284–285. Full fluorescence development was complete within 10 to 30 min at which time the gel was photographed under long wavelength ultraviolet light using Polaroid (ASA 40) Polachrome 35 mm slide film with an ultraviolet filter. Color prints (3 × 5 inches) of the slides were produced by a local commercial film processor. Relative fluorescence intensity of the gel was measured as transmittance through these prints using a scanning densitometer (Model SL-TRFF, Bio-Med Instruments, Fullerton, Calif.) equipped with a tungsten lamp and a 465 nm blue filter. This protocol gave much better results than scanning the gel itself (fluorescence diminished with time) or using either color or monochromatic Polaroid print film which was insensitive to the emission wavelength of the fluorescent derivative from o-phthalaldehyde.

Where product was measured by liquid scintillation counting, 2 cm square segments of the image gel around and including each sample well were melted at 65° C. in the presence of 0.5 ml of either 3 M $NH_4OH$ (for AG 50W-containing gels) or 3 M acetic acid (for AG 1-containing gels). After cooling, the melted segments were mixed with 20 ml of liquid scintillation fluid and counted with a Beckman Instruments (Fullerton, Calif.) Model LS 7500 liquid scintillation counter. Counts were corrected for quenching using internal standard.

Method B

Samples of glutaminase in 1% (w/v) bovine serum albumin were subjected to electrophoresis at 4° C. in a 12% (w/v) starch gel (12 × 15 × 1.2 cm) in 15 mM Tris-citrate buffer, pH 7.8 (200 V, 4 h). Sodium borate, pH 8.7, was the running buffer. Following completion of the run, the gel was sliced transversely into 2 mm thick slices for blotting.

A 2 mm thick image gel consisting of 1.5% (w/v) agarose with 49 mg/ml AG 1-X8 acetate was prepared separately as described under Method A, and a laminate of dry absorbent filter paper (Whatman 3 MM), the image gel, the slice of electrophoresis gel, and Whatman 3 MM soaked in substrate (25 mM L-glutamine in 100 mM sodium acetate, pH 4.9) was assembled as shown in FIG. 1. The assembled laminate was then wrapped in plastic wrap to prevent evaporation. The absorbent filter paper on the bottom drew substrate into the electrophoresis gel, where the enzyme catalyzed the reaction. After 1 h at room temperature, the laminate was unwrapped and the filter papers were removed. The two gels were placed, image gel toward the vacuum source, on a slab gel dryer (Model 1140, Hoefer Scientific Instruments, San Francisco, Calif.) and vacuum was applied without heat for 20 min to draw the products of the enzyme reaction into the image gel. The image gel was then separated from the electrophoresis gel and treated as described under Method A, beginning with the washing step.

RESULTS

Principle of Selective Blotting

Product-selective blotting depends on (1) quantitative transfer of low molecular weight substances between gels without excessive lateral diffusion, and (2) selective binding of the product to the binding material in the image gel, sufficiently strong so that unbound substances which would also be detected can be removed without loss of the bound material. As a model to demonstrate fulfillment of these criteria, known amounts of a glutamate standard were added to zero-time glutaminase or GOGAT reaction mixtures and replicate samples were applied to Method A blot systems. Fluorescence was observed in discrete spots which were 2 to 4 mm greater in diameter than the wells used to apply the sample.

The total fluorescence intensity (minus background) of spots from standard glutamate samples in two replicate blots done in the presence of glutaminase reaction components were proportional to the amounts of glutamate applied (R>0.9); however, values obtained from replicate samples and blots were extremely variable (30%). Possible sources of variability include (a) differences in efficiency of transfer and/or staining caused by variations in gel permeability (b) differences in photographic processing in going from slides to prints (this would only account for differences in replicate blots), and (c) uneven illumination of the gel when photographing fluorescence. Efficiency of transfer does appear to be relatively important as similar experiments done with radioactive glutamate standards showed a 15% variation in recovery (mean recovery=34%) of radioactivity in the image gel. There could be similar effects on staining. Whereas differences in illumination could lead to large discrepancies in fluorescence measurements, our measurements were done under conditions designed to minimize these effects. Nonetheless, small differences which might contribute to the overall variation may still have been present.

Similar experiments were performed in which the application layer was eliminated and radioactive glutamate standards were applied directly to the image gel in the presence of complete glutaminase reaction mixtures. Measurement of radioactivity by liquid scintillation counting showed consistent recovery (67%), with greatly improved reproducibility.

An identical set of experiments in which glutamate standards were blotted in the presence of GOGAT reaction components gave similar results for both fluorimetric and radiometric detection systems. Product-selective blots of radioactive glutamate standards into image layers in which AG 1 resin was replaced by the cation exchanger AG 50W were similar (recovery was 80%). Together, these results demonstrate the principle and utility of product-selective blotting for separating and measuring products present in enzyme reaction mixtures and emphasize that the quantitative accuracy of the results is dependent on the blotting and detection methods used.

Measurement of Enzyme Activity by Method A

To extend the principle to measurement of enzyme activities, a series of glutaminase reactions were run with varied time and enzyme concentration, and aliquots from each assay mixture were treated, along with a set of glutamate standards, according to Method A. Table 2 shows that each assay gave measurements which were not only proportional to enzyme concentration and to reaction time, but also similar to those obtained using a conventional radiometric assay.

| | | Glutamate Detected, nmols | |
|---|---|---|---|
| Glutaminase applied, mU | Time, Min. | Product-Selective Blot | Conventional Assay |
| 80 | 10 | 856 | 813 |
| 40 | 10 | 316 | 444 |
| 40 | 20 | 705 | ND[a] |
| 40 | 10 | 471 | 444 |
| 40 | 5 | 105 | ND |

[a]Not determined.

Similar experiments were performed with GOGAT. Table 3 shows a comparison of a product-selective blot with the conventional radiometric assay. Again, the glutamate detected was proportional to the amount of extract, and to the reaction time; the slightly low value at 60 min was also observed with conventional assays (separate experiment, not shown) and was probably due to a slow inactivation of the enzyme during extended incubation. For unknown reasons, activity estimates from the blot were about two-fold higher than those from conventional assays run concurrently.

TABLE 3

| Detection of GOGAT activity by a fluorimetric product-selective blot. | | | |
|---|---|---|---|
| | | Glutamate Detected, nmols | |
| GOGAT applied, µl | Time, Min. | Product-Selective Blot | Conventional Assay |
| 100 | 30 | 727 | 493 |
| 50 | 30 | 434 | 252 |
| 50 | 60 | 592 | ND[a] |
| 50 | 30 | 452 | 252 |
| 50 | 15 | 197 | — |

[a]Not determined.

Satisfactory results have also been obtained from experiments which tested the measurement of GOGAT activity by a product-selective blot in which radioactive α-ketoglutarate was used as the substrate. Radioactive glutamate formed during the reaction was separated from the substrate by direct application to an image gel containing AG 50W-X8. Liquid scintillation counts on melted segments of the image gel around each sample zone (Table 4) showed dependence on enzyme and substrate (glutamine); the activity estimates were approximately the same as those obtained by the conventional chromatography work-up. The major drawback was the incomplete washing out of background radioactivity (see values in the absence of enzyme or glutamine) which detracts from the potentially high sensitivity of the radiometric assay. Inefficient washing may be related to the increased thickness and presence of wells in the image gel set up for direct application. Direct application was chosen for this radiometric product-selective blot since it led to better recovery of glutamate and consequently to higher accuracy (see previous section). In spite of the drawback of high background levels, these data show that binding materials other than AG 1 and highly sensitive and specific radiometric assay systems may be used with the product-selective blot.

| GOGAT applied, µl | Radioactivity Detected, cpm | |
|---|---|---|
| | Product-Selective Blot | Conventional Assay[b] |
| 0 | 4882; 5497 | 200 |
| 25 | 6020; 5596 (934)[a] | 1335; 1235 (1085)[a] |
| 50 | 7254; 6844 (2458) | 2032; 2155 (1894) |
| 50 (-Glutamine) | 5642; 4172 | ND[c] |

[a]Values in parentheses are the mean differences of the values obtained in the absence of enzyme.
[b]Replicate samples were applied to columns of AG 50W-X8 (H+) and eluted. Values given are total radioactivity measured in each replicate eluate by liquid scintillation counting.
[c]Not determined.

Detection of Glutaminase Activity in Native Electrophorsis Gels Using Method B

Method A was developed primarily as a model in which to demonstrate the feasibility of using product-selective blotting to measure enzyme activities. We were ultimately interested in applying it to detection of enzyme activities in native electrophoresis gels (Method B).

To test this application, various amounts of glutaminase activity were applied to a starch gel and subjected to electrophoresis under non-denaturing conditions. A 2 mm thick transverse slice of the starch gel was then treated according to Method B. The quantity of glutamate detected in each lane was proportional to the amount of enzyme applied to the gel. Values from replicate lanes agreed within 10%. However, the glutamate detected was only 2% of that expected from the units applied. This could be due to inefficient infusion of substrates from the substrate-containing paper into the electrophoresis gel, or due to loss of activity during electrophoresis. It is notable that the addition of bovine serum albumin to the glutaminase preparation before electrophoresis was necessary for the detection of any activity. The low values are not likely to have resulted from inefficient transfer of glutamate from the electrophoresis gel to the image gel, as glutamate standards applied to the electrophoresis gel following the reaction (and before blotting) gave fluorescence measurements comparable to those obtained in Method A blots where typical recovery was 34%.

Although the foregoing invention has been described in some detail by way of illustration and example for purposes of clarity of understanding, it will be obvious that certain changes and modifications may be practiced within the scope of the appended claims.

What is claimed is:

1. A method for detecting an enzyme in a sample, said method comprising:
   reacting the sample with substrate for the enzyme in an aqueous reaction mixture so that a product is produced if enzyme is present in the sample;
   passing the reaction mixture transversely through an image gel having an immobilized phase capable of selectively binding said product but not substrate;
   washing the image gel to remove the substrate and other non-bound materials; and
   detecting the presence of said product in the image gel.

2. A method as in claim 1, wherein the enzyme is separated by gel electrophoresis from other substances in the sample prior to reaction with substrate.

3. A method as in claim 1, wherein the enzyme is separated by electrophoresis in a native gel prior to reaction with substrate.

4. A method as in claim 3, wherein the enzyme is exposed to substrate in the native electrophoresis gel and the resulting reaction mixture is transferred to the image gel by placing the electrophoresis gel against the image gel and drawing the reaction mixture from the electrophoresis gel into the image gel.

5. A method as in claim 4, wherein the reaction mixture is drawn from the electrophoresis gel to the image gel by blotting with a bibulous medium.

6. A method as in claim 4, wherein the reaction mixture is drawn from the electrophoresis gel to the image gel by means of a vacuum.

7. A method as in claim 4, wherein the reaction mixture is transferred from the electrophoresis gel to the image gel by electroblotting.

8. A method as in claim 1, wherein the product in the image gel is detected colorimetrically.

9. A method as in claim 1, wherein the product in the image gel is detected fluorescently.

10. A method as in claim 1, wherein the product in the image gel is detected radiometrically.

11. A method as in claim 1, wherein the immobilized phase is an ion exchange resin, and the reaction mixture is passed through the image gel at a pH selected to permit binding of the product but not the substrate by the ion exchange resin.

12. A method for screening a plurality of samples for the presence of an enzyme, said method employing an image gel having an immobilized phase capable of selectively binding an enzyme product but not enzyme substrate, said method comprising:
   reacting the samples suspected of containing an enzyme with the enzyme substrate of form reaction mixtures;
   applying individual reaction mixtures to one face of the image gel in a predetermined, non-overlapping pattern;
   passing the reaction mixtures transversely through the image gel in a manner such that the individual reaction mixtures do not combine, whereby said enzyme product, if any, is bound within the gel at the location corresponding to that where the reaction mixture including the product was applied;
   washing the image gel to remove the substrate and other non-bound substances; and
   detecting the presence of product within the image gel.

13. A method as in claim 12, wherein the samples are placed in an application gel having a plurality of reaction wells formed therein, wherein the application gel is free from the immobilized phase and formed directly over the image gel.

14. A method as in claim 13, wherein the reaction mixtures are drawn from the application gel to the image gel by means of a vacuum.

15. A method as in claim 12, wherein the product in the image gel is detected colorimetrically.

16. A method as in claim 12, wherein the product in the image gel is detected fluorescently.

17. A method as in claim 12, wherein the product in the image gel is detector radiometrically.

18. An assay kit for detecting an enzyme, said kit comprising:

an application gel having a plurality of wells for receiving a plurality of samples suspected of containing the enzyme;

an image gel laminated to the application gel and having an immobilized phase dispersed therein for selectively binding a product resulting from reaction of a substrate with said enzyme but not said enzyme substrate; and means for packaging the application gel and image gel.

* * * * *